(12) United States Patent
Skipworth et al.

(10) Patent No.: US 7,126,029 B2
(45) Date of Patent: Oct. 24, 2006

(54) METHOD AND APPARATUS FOR IN-PROCESS HANDLING OF CUMENE HYDROPEROXIDE WITH IMPROVED SAFETY

(75) Inventors: James G. Skipworth, Franklin Furnace, OH (US); James M. Delabar, Wheelersburg, OH (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 516 days.

(21) Appl. No.: 10/769,934

(22) Filed: Feb. 2, 2004

(65) Prior Publication Data

US 2005/0171387 A1 Aug. 4, 2005

(51) Int. Cl.
*C07C 45/00* (2006.01)
*C07C 37/08* (2006.01)

(52) U.S. Cl. ...................................... 568/385; 568/798

(58) Field of Classification Search ...................... None
See application file for complete search history.

(56) References Cited

U.S. PATENT DOCUMENTS 2,432,362 A  12/1947  Worn et al. ................. 257/234
6,225,513 B1  5/2001  Zakoshansky et al. ...... 568/798
6,307,112 B1  10/2001  Weber et al. ............... 568/798

FOREIGN PATENT DOCUMENTS

| DE | 10111889 | 10/2002 |
| EP | 0 458 149 B1 | 8/1995 |
| EP | 1 350 782 A1 | 10/2003 |

OTHER PUBLICATIONS

Perry's Chemical Engineers' Handbook Seventh Edition, 1997, pp. 11-33 to 11-45.
XP-002332166, Pellegrini, Laura et al., Italy, 2003.
XP-002332167, Pellegrini, Laura et al, Italy, 2002.

*Primary Examiner*—Sikarl A. Witherspoon
(74) *Attorney, Agent, or Firm*—Robert A. Koons, Jr.; Matthew P. McWilliams; Drinker Biddle & Reath LLP

(57) ABSTRACT

The present invention provides a method and apparatus for in-process handling of concentrated cumene hydroperoxide ("CHP") in a process for the production of phenol and acetone by the decomposition of CHP. The method of the present invention makes use of a tube and shell type heat exchanger as a vessel to accumulate a working volume of concentrated CHP from a distillation unit. Concentrated CHP is then fed to a decomposer unit from the accumulated working volume. Use of a tube and shell type heat exchanger improves safety over designs that make use of an unmodified tank or drum.

11 Claims, 3 Drawing Sheets

METHOD AND APPARATUS FOR IN-PROCESS HANDLING OF CUMENE HYDROPEROXIDE WITH IMPROVED SAFETY

FIELD OF THE INVENTION

The current invention is drawn to the field of the production of phenol and acetone by the decomposition of cumene hydroperoxide. More specifically, the present invention is drawn to a method for the safe handling of concentrated cumene hydroperoxide in a process for production of phenol and acetone by the decomposition of cumene hydroperoxide.

BACKGROUND OF THE INVENTION

The production of phenol and acetone by decomposition of cumene hydroperoxide is well known and has been in practiced commercially since the 1950's. Cumene hydroperoxide (CHP) itself is produced from the oxidation of cumene in a so-called oxidizer unit. The CHP thus produced is then concentrated in a distillation unit, typically to a concentration of 60% to 92% depending on the process. The concentrated CHP is then fed a decomposer (or cleavage) unit, where the acid decomposition of the CHP to phenol, acetone and other products such as alpha-methylstyrene occurs. In many cases, the concentrated CHP is diluted with cumene, acetone or water prior to being fed to the decomposer.

In some process designs it is desirable to accumulate a working volume of concentrated CHP from the distillation unit in an intermediate accumulation vessel and supply the decomposer unit from this working volume rather than directly from the distillation unit. In this design, the accumulated working volume is constantly turned over as concentrated CHP is fed from the accumulation vessel to the decomposer unit and fresh material is received by the accumulation vessel from the distillation unit.

The goal of accumulating a working volume to supply the decomposer is to provide a source of concentrated CHP to the decomposer unit in the event that an upset in the oxidizer and/or distillation unit temporarily interrupts the production of concentrated CHP. This is especially important in processes that conduct the decomposition of CHP in a boiling medium, where start-up or restart of the process after an upset is a hazardous operation. Even in non-boiling processes it can be of benefit to supply a working volume of concentrated CHP to avoid cavitation of pumps and transfer lines in the event of an interruption of the supply of CHP from the oxidizer and/or distillation unit.

Even though it is recognized as desirable to accumulate a working volume of concentrated CHP as described, this practice in itself presents special hazards. The decomposition of concentrated CHP is an extremely exothermic reaction, releasing approximately 1,421,000 joules/kg of heat for an 80 percent by weight solution. In some designs several thousand gallons of concentrated CHP may be accumulated. The potential for a catastrophic release of energy in the event of a mishap is therefore of great concern. A number of existing methods of accumulating working volumes of concentrated cumene hydroperoxide are not adequate to address this safety issue.

In a typical configuration for a process utilizing a boiling CHP decomposition unit, the accumulated volume of previously cooled CHP is simply stored in an unmodified tank or drum while only allowing a fraction of the accumulated volume to be used as a true working volume. In such designs the majority of the stored material exists as a stagnant volume with no circulation or mixed flow except for the natural in and out flow. Further such designs do not provide a means for direct cooling of the stored volume.

It would therefore be desirable to provide a method for storing a working volume of concentrated cumene hydroperoxide that alleviates the safety issues associated with storing extremely large volumes of stagnant concentrate without cooling.

SUMMARY OF THE INVENTION

The present invention provides an improved method for accumulation of a working volume of concentrated cumene hydroperoxide (CHP) in a process for the production of phenol and acetone by the acid catalyzed decomposition of CHP. The method of the current invention alleviates the safety issues associated with many current designs for accumulation of a working volume of concentrated CHP.

The method according to the current invention achieves this improvement through the use of a tube and shell type heat exchanger as the accumulation vessel in place of the unmodified tank or drum employed in typical designs. The heat exchanger may be oriented in either a vertical or horizontal position depending on the requirements and space constraints of a particular plant design. In a preferred embodiment the heat exchanger is a u-tube type heat exchanger and is oriented in a vertical position. The tube pitch of the heat exchanger can be varied depending on the requirements of a particular plant, but is typically about 2 inches.

Further the heat exchanger may be installed so that the concentrated CHP is carried on either the shell side or the tube side of the heat exchanger, with the heat transfer fluid carried on the tube side or shell side respectively in each case. Preferably, the concentrated CHP is carried on the shell side of the heat exchanger, with the heat exchange fluid carried on the tube side. Where the concentrated CHP is carried on the shell side of the heat exchanger, the interior of the heat exchange shell may be equipped with baffles, which induce a mixed flow of the accumulated volume through the heat exchanger.

Additionally, the heat exchanger/accumulation vessel is preferably equipped with at least one temperature sensor and at least one level sensor.

By substituting a tube and shell heat exchanger for the unmodified tank or drum used in typical designs, it is possible to apply constant cooling to the accumulated working volume of concentrated CHP. Further, by providing baffles on the interior of the heat exchanger, a mixed flow is induced in the accumulated material as it moves through the heat exchanger. Also, by its very design the tube and shell heat exchanger allows the entire accumulated volume to be used as working volume, thereby eliminating large quantities of stagnant material inherent in current designs.

DETAILED DESCRIPTION OF THE INVENTION

By utilizing a tube and shell type heat exchanger in place of the unmodified drum or tank used as an accumulation vessel for a working volume of concentrated CHP in typical current designs, the method according to the current invention alleviates a number of hazards inherent in current designs.

First, the use of a tube and shell heat exchanger according to the current invention allows constant direct cooling to be applied to the working volume of concentrated CHP. Second, by providing baffles on the interior of the tube and shell heat exchanger, a winding path of flow may be created for the concentrated CHP when it is carried on the shell side of the heat exchanger, which induces a mixed flow in the accumulated volume as it moves through the accumulation vessel. Third, because the entire volume stored in the tube and shell heat exchanger can be used as a working volume, the total accumulated volume necessary is less than in current designs.

The actual working volume of concentrated CHP that is accumulated in the accumulation vessel will depend on the requirements of the particular plant in which the method according to the current invention is carried out. However, the accumulated working volume should generally be sufficient to provide an uninterrupted supply of concentrated CHP to a decomposer unit for a minimum of 2.5 minutes at the typical feed rate for the decomposer unit involved in the event of an interruption of the supply of concentrated CHP from the distillation unit. Therefore the size and dimensions of the heat exchanger used in a particular application of the method according to the current invention will vary depending the requirements of the process and plant involved. Concentrated CHP as used in the method of the current invention is typically in the range of about 60 percent to about 92 percent by weight cumene hydroperoxide.

The selection of materials of construction for a heat exchanger to be used in the method according to the present invention is within the ability of one of ordinary skill in the art in phenol production. However, the preferred material of construction is stainless steel. Grades of stainless steel that are useful as materials of construction include, but are not limited to, 304SS and 316SS.

Figure 1:
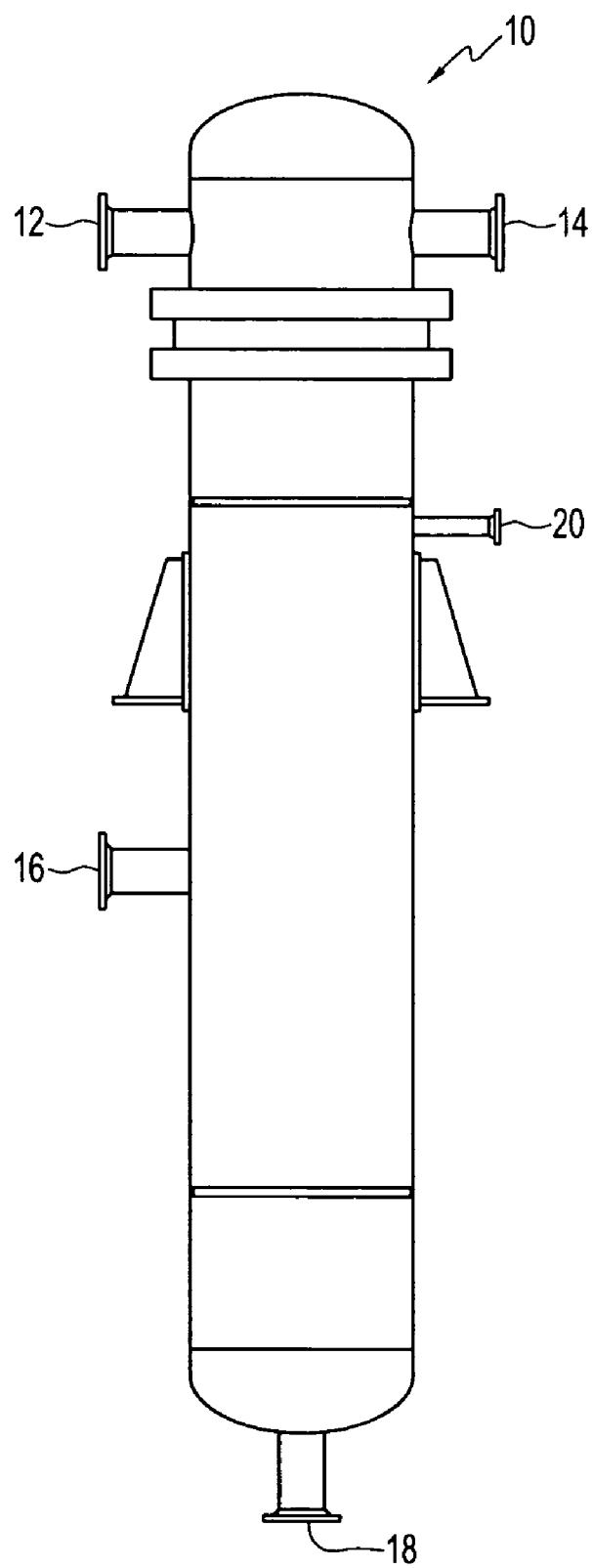
FIG. 1: Illustrates an exemplary tube and shell type heat exchanger that can be employed as an accumulation vessel according to the current invention.

Referring to FIG. 1, an exemplary tube and shell type heat exchanger 10 that may be used according to the current invention is shown. The heat exchanger 10 is essentially cylindrical in shape and is provided with inlet 12 for admitting heat exchange fluid to the tube bundle and outlet 14 for returning heat exchange fluid exiting the tube bundle to the cooling loop. The heat exchanger 10 is further provided with inlet 16 for admitting concentrated CHP from a distillation unit to the shell side of the heat exchange unit. Outlet 18 is provided for transferring concentrated CHP from a working volume to a CHP decomposer (cleavage) unit. Outlet 20 is provided as a pressure vent. As stated, the size and dimensions of a heat exchanger used in a particular implementation of the method according to the current invention will vary, and choice of an appropriate heat exchanger is within the ability of a skilled engineer.

The heat exchanger 10 in FIG. 1 is illustrated in the preferred orientation according to the current invention. That is, with the major axis of the heat exchanger oriented in the vertical direction. Also according to the preferred embodiment of the current invention, the heat exchanger is a u-tube type heat exchanger, although other configurations of the tube bundle are considered within the scope of the invention. Alternatively, the heat exchanger may be oriented with the major axis in the horizontal position. In this alternative embodiment the locations of the inlets and outlets for the heat exchange fluid and the concentrated CHP would be rearranged accordingly.

Both the CHP and the heat exchange fluid may be carried on either the shell side or the tube side of the heat exchanger according to the current invention. However, in the preferred embodiment of the invention the concentrated CHP is carried on the shell side of the heat exchanger and the heat exchange fluid is carried on the tube side.

Figure 2:
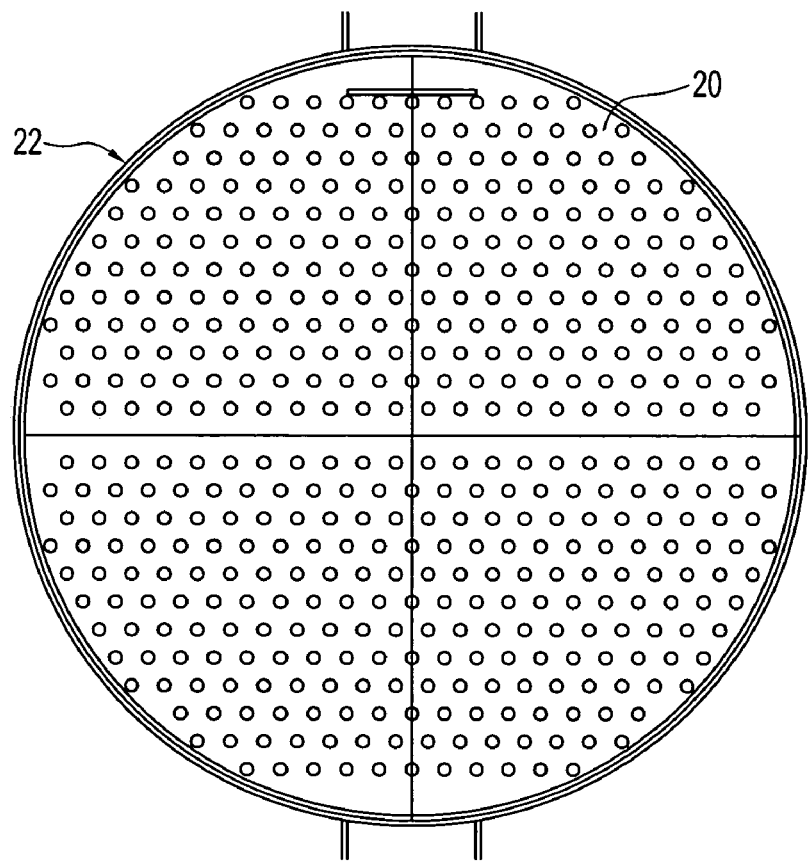
FIG. 2: Illustrates an overhead view of a tube bundle in an exemplary tube and shell type heat exchanger that can be employed according to the current invention.

Referring to FIG. 2, an overhead view of the tube bundle 20 of an exemplary u-tube type heat exchanger 22 according to the preferred embodiment of the invention is illustrated. The tube bundle 20 is laid out in the disk defined by the circumference of the heat exchanger 22.

The tube pitch in any of the tube and shell heat exchangers used according to the current invention may be set at a higher pitch than standard heat exchangers of a tube and shell type. This allows for a greater working volume of CHP to be accumulated when the CHP is carried on the shell side than would be possible in a standard tube and shell heat exchanger of similar size. The tube pitch, i.e. the spacing of the individual tubes in the bundle can however be varied depending on the size of the heat exchanger, the desired working volume and the rate of flow of CHP through it. An exemplary tube pitch according to the current invention is about 2 inches. The tube pitch is an installation specific variable that can be adjusted depending on the requirements of the plant where the method according to the invention is carried out. If an installation requires a short, squat exchanger, an increased pitch may be used to address vessel volume needs. If an installation uses a longer heat exchanger, the tube pitch may be decreased in order to reduce the volume of CHP otherwise inventoried at a higher tube pitch.

Figure 3:
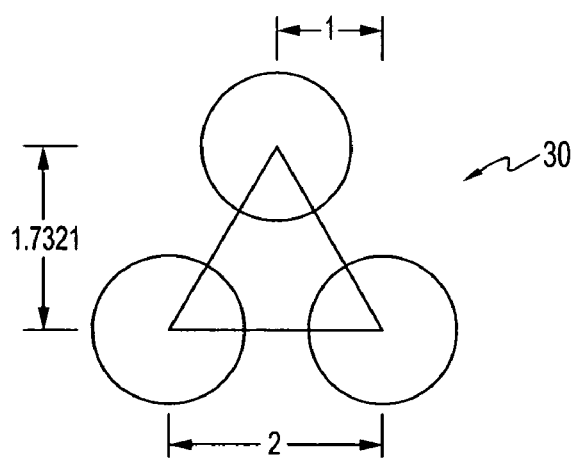
FIG. 3: Illustrates the measurement of tube pitch in a tube and shell heat exchanger.

Referring to FIG. 3, a triangle 30 connecting three adjacent tubes in a tube bundle is illustrated. The tube pitch is measured as the distance separating the center point of two adjacent tubes in the tube bundle.

Figure 4:
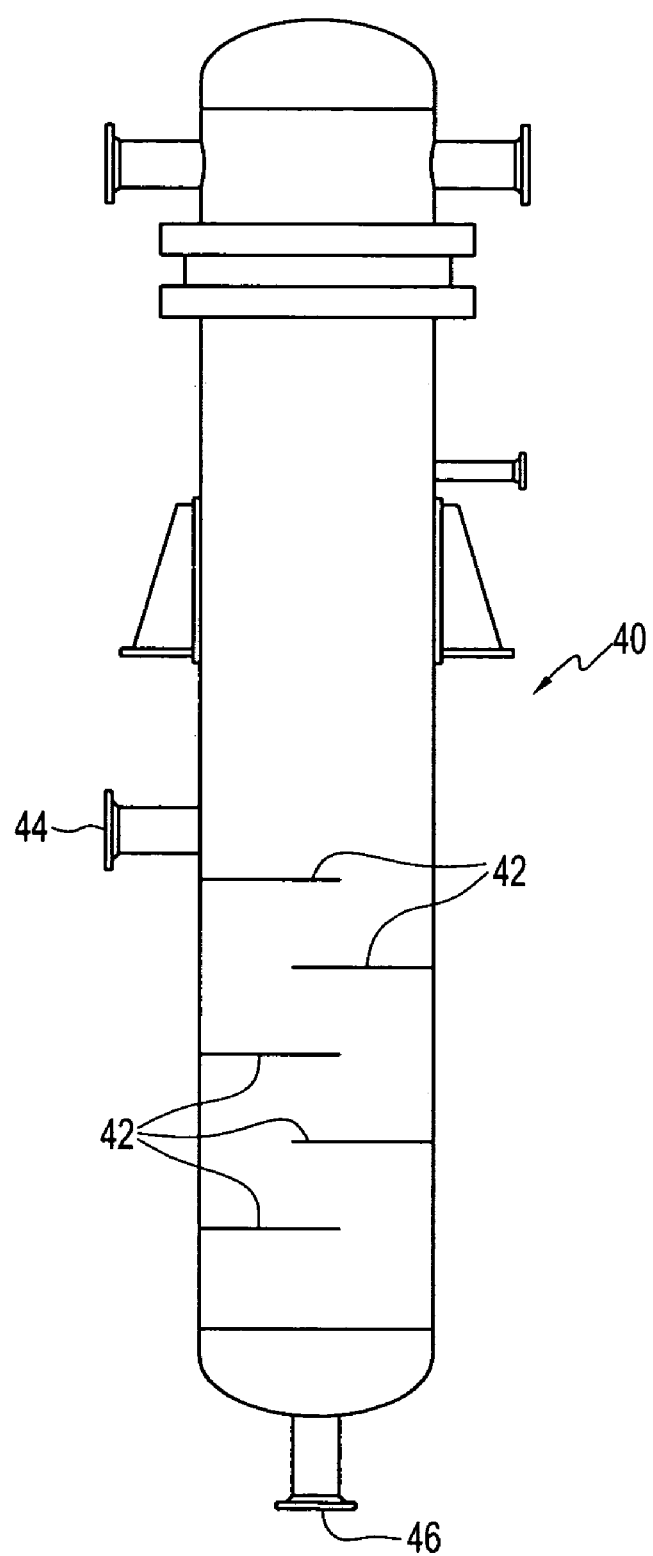
FIG. 4: Illustrates a cross-section of an exemplary tube and shell type heat exchanger that can be employed as an accumulation vessel according to the current invention.

Referring to FIG. 4, a cross section of a u-tube type heat exchanger 40 that may be used according to a preferred embodiment of the current invention is shown. The u-tubes have been omitted from the drawing for clarity. As shown in FIG. 4, preferably the heat exchanger 40 used according to the current invention is equipped with internal baffles 42. The baffles 42 create a winding path for the concentrated CHP as it travels from the inlet 44 of the heat exchanger to its outlet 46. By creating a winding path for the CHP as it travels through the heat exchanger, a mixed flow can be induced in the CHP. The number of baffles provided in the heat exchanger will vary depending on the needs of a particular process, but the number and spacing should be sufficient to provide a winding path of flow for the CHP. The determination of the number of baffles required to provide a winding path of flow is within the ability of a skilled engineer. The goal is to minimize the number of baffles, yet still provide winding flow. The actual number and spacing of baffles required will depend upon the dimensions of the installed heat exchanger, a long shell heat exchanger will require more baffles than a shorter vessel.

In addition, it may be desirable to provide the tube and shell heat exchanger with at least one level sensor and at least one temperature sensor.

The method according to the current invention has thus been described in general terms. Those of ordinary skill in the art will be able to modify and adapt the teachings of the present disclosure to suit the needs of a particular plant for the production of phenol by the acid catalyzed decomposition of CHP without departing from the present invention. All such modifications and adaptations are considered within the scope of the present invention, which is defined by the claims appended hereto.

What is claimed is:

1. An improved method for accumulating a working volume of concentrated cumene hydroperoxide in a continuous process for the production of phenol and acetone from the decomposition of cumene hydroperoxide, wherein concentrated cumene hydroperoxide is continuously fed from a distillation unit to an accumulation vessel, and from said accumulation vessel to a decomposer unit, the improvement comprising:
    providing an accumulation vessel between said distillation unit and said decomposer unit, said accumulation vessel being a tube and shell heat exchanger;
    feeding concentrated cumene hydroperoxide from said distillation unit to said accumulation vessel such that a working volume of concentrated cumene hydroperoxide is accumulated in said accumulation vessel;
    keeping said working volume of concentrated cumene hydroperoxide in a constant state of mixed flow;
    applying direct cooling to said working volume of concentrated cumene hydroperoxide; and
    feeding concentrated cumene hydroperoxide to said decomposer unit from said working volume of concentrated cumene hydroperoxide.

2. The improved method according to claim 1, wherein the major axis of said intermediate accumulation vessel is oriented vertically.

3. The improved method according to claim 2, wherein said intermediate accumulation vessel is a u-tube type heat exchanger.

4. The improved method according to claim 1, wherein the major axis of said intermediate accumulation vessel is oriented horizontally.

5. The improved method according to claim 1, wherein said working volume of concentrated cumene hydroperoxide is accumulated on the shell side of said tube and shell heat exchanger.

6. The improved method according to claim 5, wherein the interior of said tube and shell heat exchanger is baffled.

7. The improved method according to claim 1, wherein said working volume of concentrated cumene hydroperoxide is accumulated on the tube side of said tube and shell heat exchanger.

8. The improved method according to claim 1, wherein said intermediate accumulation vessel is equipped with a least one level sensor.

9. The improved method according to claim 1, wherein said intermediate accumulation vessel is equipped with a least one temperature sensor.

10. The improved method according to claim 1, wherein said intermediate accumulation vessel is fabricated from stainless steel.

11. The improved method according to claim 1, wherein the tube pitch of said tube and shell heat exchanger is about 2 inches.

* * * * *